(12) United States Patent
Kim et al.

(10) Patent No.: US 9,636,343 B2
(45) Date of Patent: May 2, 2017

(54) COMPOSITION FOR PREVENTING AND TREATING ACETAMINOPHEN INDUCING HEPATOTOXICITY CONTAINING TNP(N2-(M-TRIFLUOROBENZYL), N6-(P-NITROBENZYL)PURINE) AS AN EFFECTIVE INGREDIENT

(71) Applicant: Korea Advanced Institute of Science and Technology, Daejeon (KR)

(72) Inventors: Seyun Kim, Daejeon (KR); Yong-Mahn Han, Daejeon (KR); Young-Ran Kim, Daejeon (KR); Seulgi Lee, Cheonan-si (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/032,295

(22) PCT Filed: Jul. 3, 2015

(86) PCT No.: PCT/KR2015/006876
§ 371 (c)(1),
(2) Date: Apr. 26, 2016

(87) PCT Pub. No.: WO2016/129760
PCT Pub. Date: Aug. 18, 2016

(65) Prior Publication Data
US 2016/0354378 A1 Dec. 8, 2016

(30) Foreign Application Priority Data
Feb. 13, 2015 (KR) .................. 10-2015-0022315
Jun. 22, 2015 (KR) .................. 10-2015-0088220

(51) Int. Cl.
*A61K 31/52* (2006.01)

(52) U.S. Cl.
CPC .................................. *A61K 31/52* (2013.01)

(58) Field of Classification Search
CPC ...................................................... A61K 31/52
See application file for complete search history.

(56) References Cited

U.S. PATENT DOCUMENTS

| | | |
|---|---|---|
| 2012/0178767 A1 | 7/2012 | Ulrich |
| 2012/0220608 A1 | 8/2012 | Belardinelli et al. |
| 2013/0064799 A1 | 3/2013 | Rana |

OTHER PUBLICATIONS

Chang et al. (2002) "Purine-Based Inhibitors of Inositol-1,4,5-trisphosphate-3-kinase," ChemBioChem 3(9):897-901.

(Continued)

*Primary Examiner* — Savitha Rao
(74) *Attorney, Agent, or Firm* — Lathrop & Gage LLP

(57) ABSTRACT

The present invention relates to a composition for the prevention and treatment of liver toxicity originated from acetaminophen comprising TNP (N2-(m-Trifluorobenzyl), N6-(p-nitrobenzyl)purine) as an active ingredient. The present inventors confirmed that TNP known as a 5-inosito pyrophosphate inhibitor suppressed apoptosis caused by acetaminophen in human embryonic stem cell-derived liver cells, mouse liver cells, and human hepatoma cell lines, up-regulated glutathione converted in liver cells, and inhibited JNK phosphorylation that is a kind of response against stress increased by acetaminophen. The inventors further confirmed that TNP had the activity of protecting liver cells from the toxicity caused by acetaminophen in an animal model. Therefore, TNP can be efficiently used as an active ingredient for a composition for the prevention and treatment of liver toxicity caused by acetaminophen.

7 Claims, 12 Drawing Sheets

(56) References Cited

OTHER PUBLICATIONS

Padmanabhan et al. (2009) "Characterization of a Selective Inhibitor of Inositol Hexakisphosphate Kinases—Use in Defining Biological Roles and Metabolic Relationships of Inositol Pyrophosphates," The Journal of Biological Chemistry 284(16):10571-10582.

Wang et al. (2014) "Aging as an Essential Modifier for the Efficacy in Mesenchymal Stem Cell Therapy Through an Inositol Phosphate 6 Kinase-Inositol Pyrophosphate 7-Dependent Mechanism," Stem Cell Research & Therapy 5(2):43 (pp. 1-2).

Figure 2
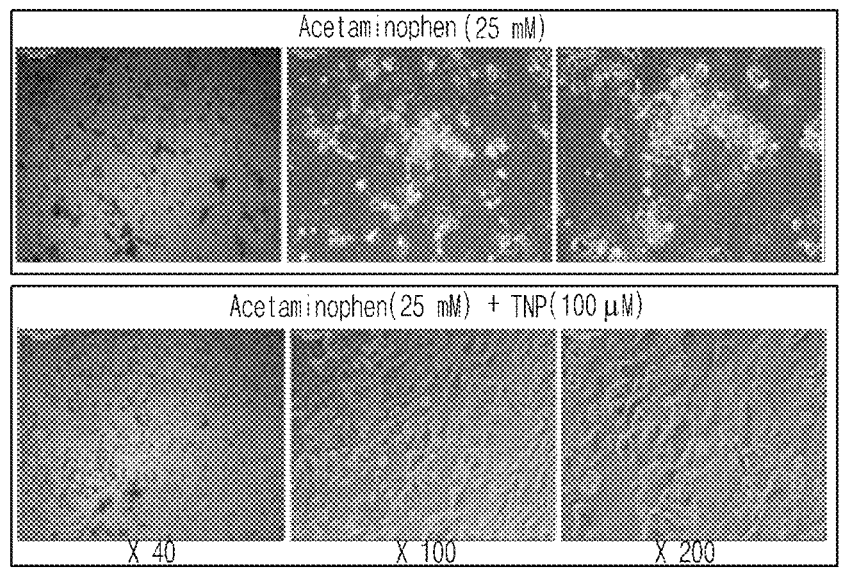
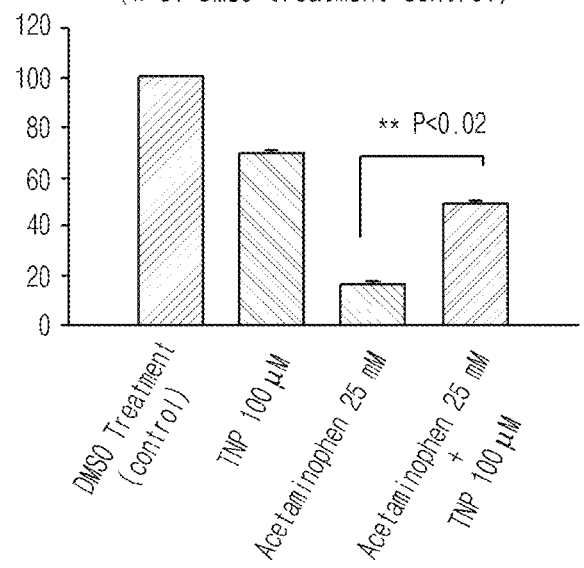

Figure 3
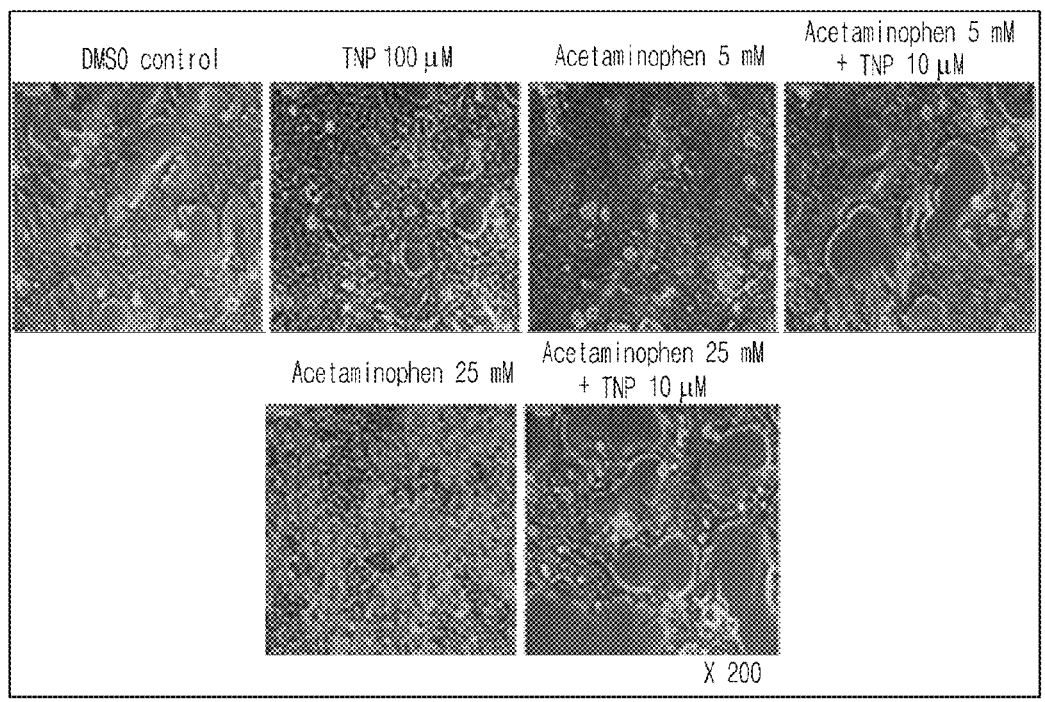
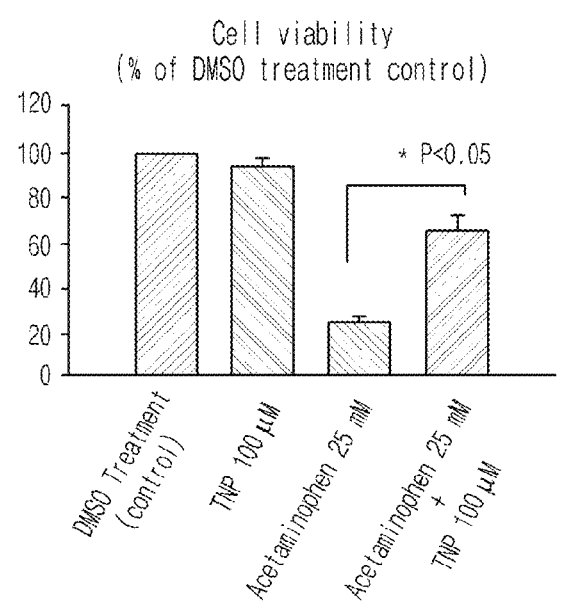

Figure 4
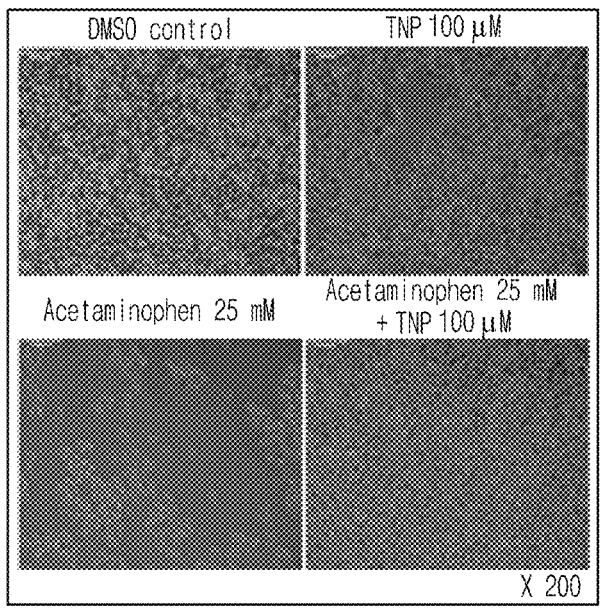
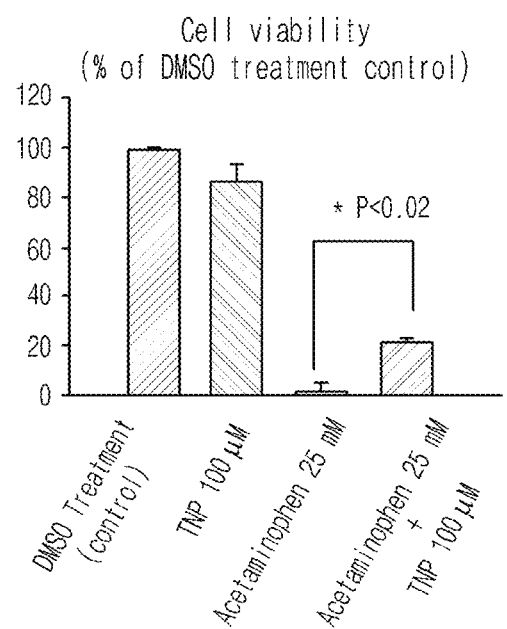

COMPOSITION FOR PREVENTING AND TREATING ACETAMINOPHEN INDUCING HEPATOTOXICITY CONTAINING TNP(N2-(M-TRIFLUOROBENZYL), N6-(P-NITROBENZYL)PURINE) AS AN EFFECTIVE INGREDIENT

CROSS-REFERENCE TO RELATED APPLICATIONS

This application is a U.S. National Stage Application filed under 35 U.S.C. §371 of International Application No. PCT/KR2015/006876, filed Jul. 3, 2015, which claims the benefit of Korean Application No. KR 10-2015-0088220, filed Jun. 22, 2015, and Korean Application No. KR 10-2015-0022315, filed Feb. 13, 2015. All of these applications are hereby incorporated by reference in their entireties.

BACKGROUND OF THE INVENTION

1. Field of the Invention

The present invention relates to a pharmaceutical composition for the prevention and treatment of liver toxicity comprising TNP (N2-(m-Trifluorobenzyl), N6-(p-nitrobenzyl)purine) or a pharmaceutically acceptable salt of the same as an active ingredient and a health functional food comprising the same.

2. Description of the Related Art

TNP (N2-(m-Trifluorobenzyl), N6-(p-nitrobenzyl)purine) is a commercialized chemical, which is known as the inositol pentakisphosphate kinase specific inhibitor (J Biol Chem. Apr. 17, 2009; 284(16): 10571-10582). TNP inhibits the biosynthesis of 5-inositol pyrophosphate, by which TNP down-regulates intracellular 5-inositol polyphosphate and at the same time increases insulin signaling in liver cells (Cell. 2010; 143(6): 897910). When TNP is treated to bone marrow derived mesenchymal stem cells, it can delay the progress of cellular aging (Stem Cell Res Ther. 2014 Mar. 26; 5(2):33). However, it is unknown whether or not TNP has the effect of preventing or treating acute liver toxicity.

Acetaminophen (AP), which is well known as Tylenol, has been developed in USA in 1950s. This drug is one of the most used drugs that has been world-widely used as a pain killer and a fever reducer (domestic Tylenol sales a year is approximately 25 million dollars). The chemical name of Tylenol is N-acetyl-p-aminophenol and is also called paracetamol (Dargan P I et al., Crit Care. 2002 6(2):108-10). The acceptable dose of acetaminophen is 150 mg/kg/day, and maximum 4 g can be orally administered to an adult for a day. So, it is classified as a safe OTC (over the counter) drug that can be sold without doctor's prescription. However, if acetaminophen is over-used, fulminant hepatic failure, liver necrosis, nephrotoxicity, and liver cirrhosis, or even death can be caused. So, it can be said that this drug has a double-sided character.

The mechanism of liver toxicity is that acetaminophen turns into a cell-killing reactive material mediated by a hepatic oxidase. In general, when such a reactive material is generated, it is detoxified without causing a problem. But, the excessive dose of such a material consumes all the endogenous antitoxic materials, leading to the destruction of liver cells. Particularly, when acetaminophen is administered at a low concentration, it binds to non-toxic gluconic acid and sulfate, resulting in the detoxified conjugate, and then it is excreted through bile or blood plasma. And 5~10% of the administered acetaminophen is metabolized by P450 (CYP) particularly by CYP2E1 (Ray S D et. al., J Pharmacol Exp Ther. 1996; 279:1470-83). That is, acetaminophen is changed into N-acetyl-p-benzoquinoneimine (NAPQI) in the liver, and the converted metabolite binds to glutathione and at this time this conjugate does not show toxicity (Hazai E, et al., Biochem Biophys Res Commun. 2002; 291(4): 1089-1094.). However, when the excessive dose of acetaminophen is taken in the liver, it binds to gluconic acid and sulfate with loosing detoxification ability and as a result highly reactive NAPQI is accumulated, by which cell membrane is critically damaged to induce apoptosis of liver cells that cannot be recovered and instead causes liver toxicity or even death (Webster P A et. al., J Clin Pharmacol. 1996; 36:397-402; Albano E et. al., Mol Pharmacology. 1985; 28:306-11; Kyle M E et. al., Biochem Biophys Res Commun. 1987; 149:889-94 Mahadevan S B et. al., Arch Dis Child. 2006: 91:598-603).

The animal models for acetaminophen mediated liver injury model are represented by the mouse model and the hamster model. Similarity is found in human (Tee L B et al., Toxicol Appl Pharmacol. 83(2):294-314. 1986). Liver toxicity caused by acetaminophen increases when alcohol is taken in together. It is mandatory by FDA to notify that a patient who regularly drinks alcohol at least three glasses of alcohol daily must consult with a doctor before taking this drug because of the liver toxicity. Studies have been actively going on to develop a drug to eliminate and relieve the liver toxicity caused by acetaminophen.

The liver is a major organ responsible for detoxication and controlling blood circulation. Once the liver is injured, various diseases can be caused along with inflammatory response. So, it is very important to develop a drug that can protect the liver from being injured.

Thus, the present inventors searched and tried to identify a material that is effective in preventing and treating liver injury. As a result, the inventors confirmed that TNP known as a 5-inositol pyrophosphate inhibitor suppressed apoptosis caused by acetaminophen in human embryonic stem cell-derived liver cells, mouse liver cells, and human hepatoma cell lines, increased the concentration of glutathione converted in liver cells, and inhibited JNK phosphorylation that is a kind of response against stress increased by acetaminophen. The inventors further confirmed that TNP had the activity of protecting liver cells from the toxicity caused by acetaminophen in an animal model. At last, the inventors completed this invention by disclosing that TNP or a pharmaceutically acceptable salt thereof could be efficiently used as an active ingredient of a composition for preventing and treating liver toxicity.

SUMMARY OF THE INVENTION

It is an object of the present invention to provide a pharmaceutical composition for the prevention and treatment of liver toxicity comprising TNP (N2-(m-Trifluorobenzyl), N6-(p-nitrobenzyl)purine) or a pharmaceutically acceptable salt thereof as an active ingredient.

To achieve the object above, the present invention provides a pharmaceutical composition for the prevention and treatment of liver toxicity comprising TNP (N2-(m-Trifluorobenzyl) N6-(p-nitrobenzyl)purine), or a pharmaceutically acceptable salt thereof as an active ingredient.

The present invention also provides a health functional food for the prevention and improvement of liver toxicity comprising TNP or a pharmaceutically acceptable salt thereof as an active ingredient.

The present invention further provides a method for treating liver toxicity containing the step of administering a pharmaceutically effective dose of TNP or a pharmaceutically acceptable salt thereof to a subject having toxic liver disease.

The present invention also provides a method for preventing liver toxicity containing the step of administering a pharmaceutically effective dose of TNP or a pharmaceutically acceptable salt thereof to a subject.

The present invention also provides a use of TNF or a pharmaceutically acceptable salt thereof for the composition for preventing and treating liver toxicity.

The present invention also provides a use of TNP or a pharmaceutically acceptable salt thereof for the health functional food for preventing and improving liver toxicity.

The present invention also provides a pharmaceutical composition for the prevention and treatment of liver disease comprising TNP or a pharmaceutically acceptable salt thereof as an active ingredient.

In addition, the present invention provides a health functional food for the prevention and improvement of liver disease comprising TNP or a pharmaceutically acceptable salt thereof as an active ingredient.

The present invention further provides a method for treating liver disease containing the step of administering a pharmaceutically effective dose of TNP or a pharmaceutically acceptable salt thereof to a subject having liver disease.

The present invention also provides a method for preventing liver disease containing the step of administering a pharmaceutically effective dose of TNP or a pharmaceutically acceptable salt thereof to a subject.

The present invention also provides a use of TNP or a pharmaceutically acceptable salt thereof for the composition for preventing and treating liver disease.

The present invention also provides a use of TNP or a pharmaceutically acceptable salt thereof for the health functional food for preventing and improving liver disease.

Advantageous Effect

The present invention relates to a composition for the prevention and treatment of liver toxicity comprising TNP (N2-(m-Trifluorobenzyl), N6-(p-nitrobenzyl)purine) or a pharmaceutically acceptable salt thereof as an active ingredient. The present inventors confirmed that TNP known as a 5-inositol pyrophosphate inhibitor suppressed apoptosis caused by acetaminophen in human embryonic stem cell-derived liver cells, mouse liver cells, and human hepatoma cell lines, up-regulated glutathione converted in liver cells, and inhibited JNK phosphorylation that is a kind of response against stress increased by acetaminophen. The inventors further confirmed that TNP had the activity of protecting liver cells from the toxicity caused by acetaminophen in an animal model. Therefore, TNP or a pharmaceutically acceptable salt thereof can be efficiently used as an active ingredient of a composition for preventing and treating liver toxicity.

BRIEF DESCRIPTION OF THE DRAWINGS

The application of the preferred embodiments of the present invention is best understood with reference to the accompanying drawings, wherein:

FIG. 2 is a set of a photograph and a graph illustrating the apoptosis according to the treatment of acetaminophen and TNP in those liver cells differentiated from human embryonic stem cells.

FIG. 3 is a set of a photograph and a graph illustrating the apoptosis according to the treatment of acetaminophen and TNP in the mouse derived liver cells.

FIG. 4 is a set of a photograph and a graph illustrating the apoptosis according to the treatment of acetaminophen and TNP in the human hepatoma cell line HepG2.

DESCRIPTION OF THE PREFERRED EMBODIMENTS

Figure 1:
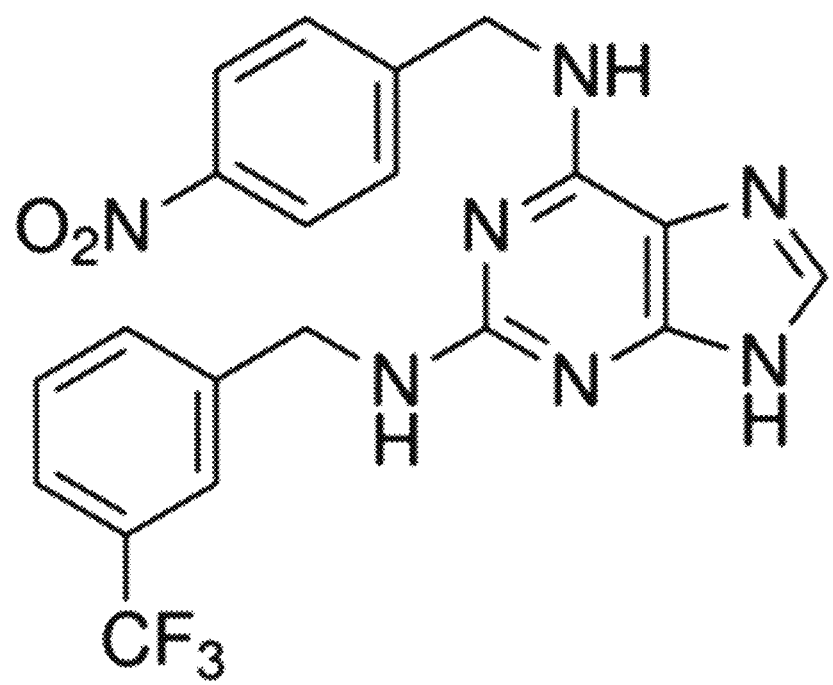
FIG. 1 is a diagram illustrating the structure of TNP (N2-(m-Trifluorobenzyl), N6-(p-nitrobenzyl)purine).

Hereinafter, the present invention is described in detail.

The present invention provides a pharmaceutical composition for the prevention and treatment of liver toxicity comprising TNP (N2-(m-Trifluorobenzyl), N6-(p-nitrobenzyl)purine) or a pharmaceutically acceptable salt thereof as an active ingredient.

The said TNP preferably has the structure represented by the following formula 1, but not always limited thereto:

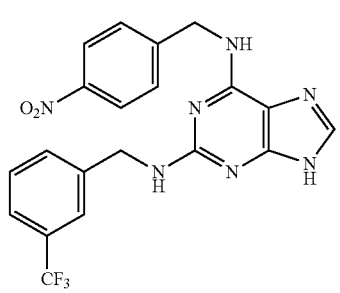

[Formula 1]

The said TNP of the present invention preferably suppresses the apoptosis caused by acetaminophen, increases the level of glutathione (GSH) in liver cells, and suppresses the reaction against acetaminophen induced stress, but not always limited thereto.

In a preferred embodiment of the present invention, the present inventors investigated the changes in acetaminophen caused apoptosis pattern according to the treatment of TNP in human embryonic stem cell-derived liver cells, mouse derived liver cells, and the human hepatoma cell line HepG2. As a result, it was confirmed that the acetaminophen caused apoptosis in liver cells was significantly suppressed by the treatment of TNP (see FIGS. 2~5). The inventors also investigated the metabolizing activity of liver cells on acetaminophen after the treatment of TNP. As a result, it was confirmed that the level of the converted glutathione in liver cells that had been decreased by acetaminophen was increased by the treatment of TNP (see FIG. 6). In the mouse derived liver cells and the human hepatoma cell line HepG2, the activity of TNP to control the reaction against acetaminophen caused stress in liver cells was investigated. As a result, it was confirmed that the phosphorylated JNK signal was increased by the stress response caused by acetaminophen, which was reversely inhibited significantly by the treatment of TNP (see FIGS. 7~8). A mouse model was treated with acetaminophen, and then administered with TNP. As a result, the individual survival rate was increased (see FIG. 9); necrosis of the liver extracted from the mouse was decreased (see FIG. 10); the levels of the liver toxicity serum indexes AST and ALT were significantly decreased (see FIG. 11); and the phosphorylated JNK was significantly inhibited (see FIG. 12).

In conclusion, the present inventors confirmed that TNP known as the 5-inositol pyrophosphate inhibitor, of the invention suppressed apoptosis caused by acetaminophen in human embryonic stem cell-derived liver cells, mouse derived liver cells, and human hepatoma cell lines; increased the level of converted glutathione in liver cells; and inhibited JNK phosphorylation that is a kind of response against stress increased by acetaminophen. The present inventors also confirmed that TNP had the activity of protecting liver cells from the toxicity caused by acetaminophen in an animal model. Therefore, TNP or a pharmaceutically acceptable salt thereof can be efficiently used as a pharmaceutical composition for the prevention and treatment of liver toxicity.

The present invention includes not only the TNP represented by formula 1 but also a pharmaceutically acceptable salt thereof, and a solvate, a hydrate, a racemate, or a stereoisomer possibly produced from the same.

The TNP represented by Formula 1 of the present invention can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt of the present invention can be prepared by the conventional method. For example, the TNP represented by formula 1 is dissolved in excessive acid aqueous solution and then the salt can be prepared by precipitation using a water-miscible organic solvent which is exemplified by methanol, ethanol, acetone, or acetonitrile. Then, the solvent or the excessive acid is evaporated from the mixture, followed by drying the mixture to give the addition salt or suction-filtering the precipitated salt to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The composition of the present invention can be formulated by mixing with generally used diluents or excipients such as fillers, extenders, binders, wetting agents, disintegrating agents and surfactants.

Solid formulations for oral administration are tablets, pills, powders, granules, capsules, and troches. These solid formulations are prepared by mixing the TNP represented by formula 1 of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories.

Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The composition of the present invention can be administered at a pharmaceutically effective dose. The term "pharmaceutically effective dose" herein indicates the amount enough to treat the disease with applicable, reasonable or risky concentration. The dose can be determined by considering many factors such as the type of disease, the severity of disease, the activity of drug, the sensitivity to drug, administration frequency and pathway, excretion, the term of treatment, co-treatment drug and other factors regarded as relevant in the medicinal field. The composition of the present invention can be administered alone as an individual therapeutic agent or co-treated with other drugs. It can be administered with the conventional drugs stepwise or simultaneously, and single or multiple administrations is allowed. It is important to determine a dose that can bring the maximum effect with the minimum amount without side effects, considering all the factors mentioned above. Such determination can be easily made by those in the art.

Particularly, the effective dose of the compound of the present invention is preferably 0.1 mg~100 mg/kg and more preferably 0.5 mg~10 mg/kg, which can be administered every day or every other day, or 1~3 times a day. However, the effective dose can be increased or decreased according to the administration pathway, severity of obesity, gender, body weight, and age of patient, etc, so that the effective dose above cannot limit the present invention in any aspects.

The present invention also provides a health functional food for the prevention and improvement of liver toxicity comprising TNP or a pharmaceutically acceptable salt thereof as an active ingredient.

The said TNP preferably has the structure represented by formula 1, but not always limited thereto:

The said TNP of the present invention preferably suppresses the apoptosis caused by acetaminophen, increases the level of glutathione (GSH) in liver cells, and suppresses the reaction against acetaminophen induced stress, but not always limited thereto.

It was confirmed that the TNP known as the 5-inositol pyrophosphate inhibitor of the invention suppressed apoptosis caused by acetaminophen in human embryonic stem cell-derived liver cells, mouse derived liver cells, and human hepatoma cell lines; increased the level of converted glutathione (GSH) in liver cells; and inhibited JNK phosphorylation that is a kind of response against stress increased by acetaminophen. It was also confirmed that TNP had the activity of protecting liver cells from the toxicity caused by acetaminophen in an animal model. Therefore, TNP or a pharmaceutically acceptable salt thereof can be efficiently used as a health functional food for the prevention and improvement of liver toxicity.

The TNP of the present invention can be prepared by the various methods well-informed in the field of food science or pharmaceutics to be used for the prevention and improvement of liver toxicity. For example, it can be formulated in any food that can be orally taken and at this time TNP can be added by itself or can be mixed with any sitologically acceptable carrier, excipient, or diluent. Preferably, it can be formulated in the form of beverages, pills, granules, tablets, or capsules.

The health functional food of the present invention can additionally include any sitologically acceptable ingredient that can be generally added to processed food. For example, in the case TNP is prepared as beverages, the beverages can include, in addition to TNP, one or more ingredients selected from the group consisting of citric acid, high fructose corn syrup, sugar, glucose, acetic acid, malic acid, and fruit juice.

The effective dose of TNP as an active ingredient of the health functional food of the present invention can be determined properly according to age, gender, weight, and condition of patient targeted for the prevention and improvement of liver toxicity, along with severity of disease, which is preferably 0.01 g 10.0 g/day/adult. By taking such a health functional food comprising the above at the recommended dose, liver toxicity can be prevented and improved.

The present invention also provides a pharmaceutical composition for the prevention and treatment of liver disease comprising TNP or a pharmaceutically acceptable salt thereof as an active ingredient.

In addition, the present invention provides a health functional food for the prevention and improvement of liver disease comprising TNP or a pharmaceutically acceptable salt thereof as an active ingredient.

The said TNP preferably has the structure represented by the following formula 1, but not always limited thereto:

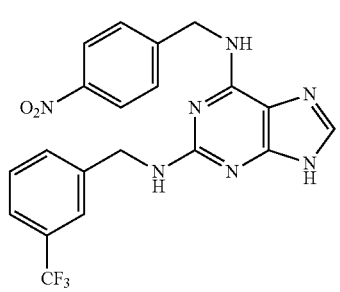

[Formula 1]

The said TNP of the present invention preferably suppresses the apoptosis caused by acetaminophen, increases the level of glutathione (GSH) in liver cells, and suppresses the reaction against acetaminophen induced stress, but not always limited thereto.

The said liver disease caused by acetaminophen is preferably selected from the group consisting of fulminant hepatic failure, liver necrosis, nephrotoxicity, and liver cirrhosis, but not always limited thereto.

It was confirmed that the TNP known as the 5-inositol pyrophosphate inhibitor of the invention suppressed apoptosis caused by acetaminophen in human embryonic stem cell-derived liver cells, mouse derived liver cells, and human hepatoma cell lines; increased the level of converted glutathione (GSH) in liver cells; and inhibited JNK phosphorylation that is a kind of response against stress increased by acetaminophen. It was also confirmed that TNP had the activity of protecting liver cells from the toxicity caused by acetaminophen in an animal model. Therefore, TNP or a pharmaceutically acceptable salt thereof can be efficiently used as a pharmaceutical composition for the prevention and treatment of liver disease and a health functional food for the prevention and improvement of liver disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Culture of Human Embryonic Stem Cell (hESC)-Derived Liver Cells

To investigate the differentiation of human embryonic stem cells into different line cells including endoderm cells, the differentiation of human embryonic stem cells into hepatocytes, the endoderm cells, was induced (Cai, J. et. al, (2007) Hepatology 45(5): 1229-1239).

Particularly, CHA-hESC cell line was cultured in the conditioned medium with feeder-free system for 3 days to be confluent. Upon completion of the culture, the hESC cells were cultured in RPMI-1640 (Hyclone, USA) supplemented with 50 ng/ml of Activin A (Peprotech, USA) for 5 days to induce the differentiation. The differentiated cells were cultured in the hepatocyte culture medium (HCM; Lonza, USA) supplemented with 30 ng/ml of fibroblast growth factor 4 (Peprotech) and 20 ng/ml of bone morphogenetic protein 2 (BMP2; Peprotech) for 5 days. Then, the cells were further cultured in the hepatocyte culture medium supplemented with 20 ng/ml of hepatocyte growth factor (HGF; Peprotech) for another 5 days to induce the differentiation of hESC into hepatocytes. The differentiated hepatocytes were cultured in the hepatocyte culture medium supplemented with 10 ng/ml of oncostatin M (R&D Systems, USA) and 0.1 μM of dexamethasone (Sigma) for 5 days to induce maturation of the hepatocytes. At last, the mature hepatocytes were obtained.

Example 2: Culture of Mouse Derived Liver Cells

Mouse derived liver cell culture was performed via collagenase perfusion as follows.

Particularly, the male C57BL/6J mouse at 10~12 weeks was anesthetized by administrating Avertin via intraperitoneal injection, and the abdomen was opened. 24 gauge catheter was inserted in the portal vein to perfuse with a perfusion solution (1.42 M Nacl, 0.067 M Kcl, 0.1 M HEPES PH 7.4, 0.05 M EGTA). Then, a digestion solution comprising collagenase (Worthington, USA) was circulated. After the liver cells were digested, the mesenteric membrane was peeled off to separate liver cells, followed by filtering with nylon mesh. The filtrate was centrifuged at 100×g for 3 minutes. The supernatant was discarded and the precipitated liver cells were suspended in HBSS buffer (Hanks' Balanced salt solution, WelGene), followed by centrifugation. The precipitated liver cells were centrifuged at 2400 rpm for 10 minutes in Percol solution (autoclaved percoll (Sigma), 10×PBS, 1 M HEPES pH 7.4). The supernatant was discarded and the precipitated liver cells were suspended in HBSS buffer (Hanks' Balanced salt solution, WelGene), followed by centrifugation again at 100×g. The precipitated liver cells were suspended in the culture medium. The obtained cell suspension was loaded in the culture vessels precoated with gelatin at the density of 1×10$^6$ cells/ml. The culture medium herein was DMEM (Biowest) supplemented with 10% FBS, 10 nM dexamethasone, 10 nM insulin, and penicillin/streptomycin (100 μg/ml). The cells were cultured in a 37° C. incubator under the control of temperature and humidity with supplying a mixed gas containing $CO_2$ by 5%.

Example 3: Culture of the Human Hepatoma Cell Line HepG2

The human hepatoma cell line HepG2 was distributed in a 6 well plate precoated with gelatin at the density of 1×10$^6$ cells/ml, followed by culture for 24 hours for cell adhesion. The culture medium herein was DMEM (Biowest) supplemented with 10% FBS, 10 nM dexamethasone, 10 nM insulin, and penicillin/streptomycin (100 μg/ml). The cells were cultured in a 37° C. incubator under the control of temperature and humidity with supplying a mixed gas containing $CO_2$ by 5%.

Experimental Example 1: Suppression of Acetaminophen Caused Apoptosis by the Treatment of TNP in Human Embryonic Stem Cell Derived Liver Cells The changes in acetaminophen caused apoptosis according to the treatment of TNP were investigated in the human embryonic stem cell-derived liver cells cultured by the same manner as described in Example 1.

Particularly, the liver cells on the 19$^{th}$ day from the differentiation from human stem cells were distributed in a 6 well plate at the concentration of 90% each well. The culture medium was replaced with DMEM (Dulbecco's Modified Eagle's Medium, No. 001-11, WelGene) containing low glucose (1000 mg/l), followed by culture for 2 hours. The cells were treated with acetaminophen alone (25 mM) and acetaminophen (25 mM) together with TNP (100 μM) for 18 hours respectively. Then, the cells were observed under microscope. This experiment was performed in triplicate and the cell survival rate was analyzed based on the results. For the cell survival rate analysis, the cell culture medium was eliminated twice by using 1 ml of PBS, followed by treatment with 1 ml of Trypsin/EDTA mixed solution (Invitrogen) for 1 min. Then, the cells were collected by pipetting. 10 ml of trypan blue and 10 ml of PBS containing the collected cells were mixed followed by analyzing cell survival rate using automated cell viability analyzer Countess (Invitrogen). All the statistic treatments in this invention were presented as mean±SD and the statistic analysis was performed by using Student's t-test. The maximum limits of significance were determined as $p<0.05$.

As a result, as shown in FIG. 2, it was confirmed that the apoptosis of liver cells caused by acetaminophen was significantly suppressed by the treatment of TNP (FIG. 2).

Experimental Example 2: Suppression of Acetaminophen Caused Apoptosis by the Treatment of TNP in Mouse Derived Liver Cells The changes in acetaminophen caused apoptosis according to the treatment of TNP were investigated in the mouse derived liver cells cultured by the same manner as described in Example 2.

Particularly, the mouse derived liver cells were distributed in a 6 well plate at the concentration of 100% each well. The cell survival rate was calculated by the same manner as described in Experimental Example 1. All the statistic treatments in this invention were presented as mean±SD and the statistic analysis was performed by using Student's t-test. The maximum limits of significance were determined as $p<0.05$.

As a result, as shown in FIG. 3, it was confirmed that the apoptosis of liver cells caused by acetaminophen was significantly suppressed by the treatment of TNP (FIG. 3).

Experimental Example 3: Suppression of Acetaminophen Caused Apoptosis by the Treatment of TNP in the Human Hepatoma Cell Line HepG2

The changes in acetaminophen caused apoptosis according to the treatment of TNP were investigated in the human hepatoma cell line HepG2 cultured by the same manner as described in Example 3.

Particularly, the human hepatoma cell line HepG2 was distributed in a 6 well plate at the concentration of 90% each well. The cell survival rate was calculated by the same manner as described in Experimental Example 1. All the statistic treatments in this invention were presented as mean±SD and the statistic analysis was performed by using Student's t-test. The maximum limits of significance were determined as $p<0.05$.

Figure 5:
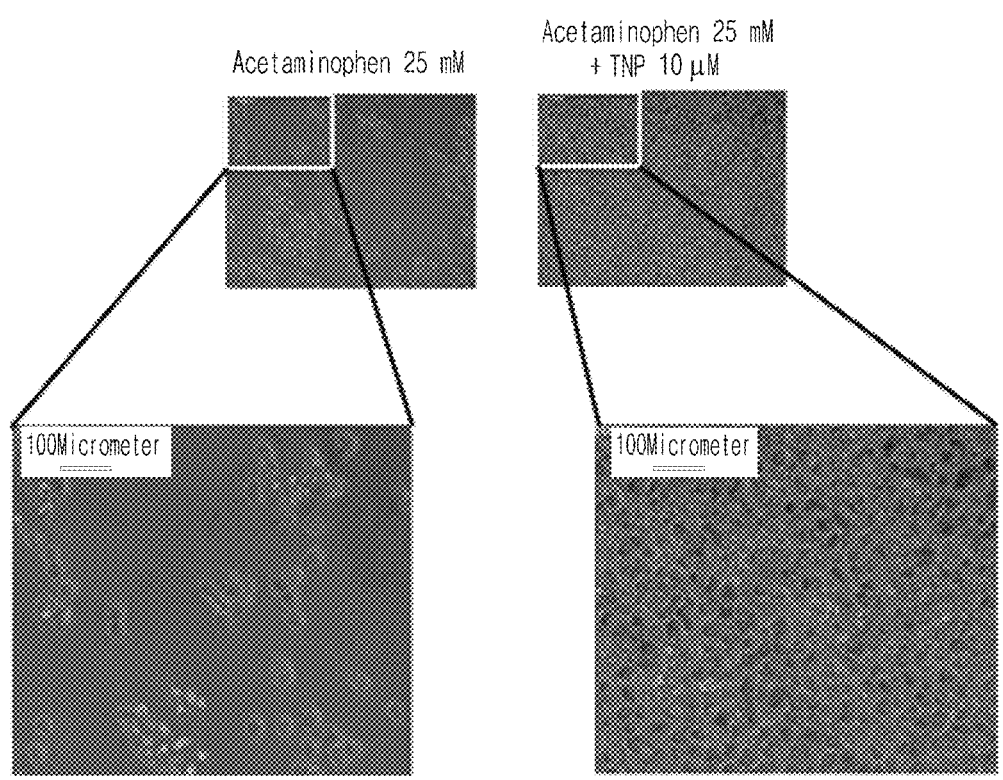
FIG. 5 is a diagram illustrating the 200 fold enlarged photo of FIG. 4.

As a result, as shown in FIG. 4 and FIG. 5, it was confirmed that the apoptosis of liver cells caused by acetaminophen was significantly suppressed by the treatment of TNP (FIGS. 4 and 5).

Experimental Example 4: Inhibitory Effect of TNP on the Decrease of Intracellular Glutathione (GSH) Caused by Acetaminophen in Mouse Derived Liver Cells The metabolizing activity of liver cells on acetaminophen according to the treatment of TNP was investigated.

Particularly, the level of the reduced glutathione (GSH) in the mouse derived liver cells treated with acetaminophen and TNP by the same manner as described in Experimental Example 2 was measured. The measurement of the reduced glutathione was performed by using GSH-Glo Glutathione Assay kit (Promega) with Tristar2 LB 942 plate reader.

Figure 6:
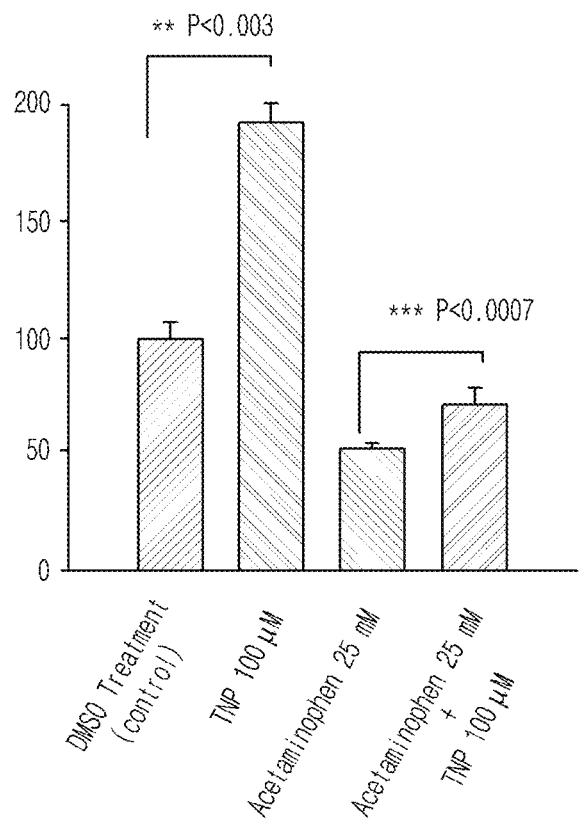
FIG. 6 is a graph illustrating the changes of the intracellular glutathione concentration according to the treatment of acetaminophen and TNP in the mouse derived liver cells.

As a result, as shown in FIG. 6, it was confirmed that the reduced glutathione concentration was increased in the liver cells by the treatment of TNP alone. In the meantime, it was also confirmed that the decrease of the reduced glutathione caused by glutathione was back to increase in the liver cells by the treatment of TNP (FIG. 6).

Experimental Example 5: Suppression of JNK Phosphorylation Increased by Acetaminophen According to the Treatment of TNP in the Mouse Derived Liver Cells The regulation of response against stress caused by acetaminophen in liver cells according to the treatment of TNP was investigated.

Particularly, the mouse derived liver cells treated with acetaminophen and TNP by the same manner as described in Experimental Example 2 were obtained. Cell extract was prepared for protein assay. Then, SDS-PAGE and Western blotting were performed. The cells were lysed in 10 ml of SDS buffer (50 mM Tris-HCl, 1% IGEPAL CA-630, 0.25% deoxycholic acid, 150 mM NaCl, 1 mM ethylene-diamine tetra acetic acid, 1 mM NaF, and 0.1% sodium dodecyl sulfate, pH 7.4) containing protease inhibitor cocktail (Complete Mini, Roche, Germany). The cell lysate was placed in ice for 20 minutes, followed by centrifugation at 4° C., at 13000 rpm, for 10 minutes. Upon completion of the centrifugation, the protein in the supernatant was quantified (Bio-Rad Laboratories, USA). 50 µg of the protein was loaded for SDS-PAGE (SDS-polyacrylamide gel electrophoresis). The electrophoresed protein was transferred onto Immobilon-P transfer membrane (Millipore Corporate, USA) by using electroblotting. The membrane was then loaded in TBS (Tris-buffered saline) containing 0.1% Tween 20 and 10% milk powder, followed by blocking for 1 hour. The phosphorylated JNK (Cell Signaling) and the whole JNK (Cell Signaling) antibody were added thereto, followed by reaction for overnight. The membrane was washed with TBS containing 0.1% Tween 20 three times for 20 minutes each. HRP (horseradish peroxidase) conjugated secondary antibody was added thereto, followed by reaction for 1 hour. Then, the membrane was washed with TBS containing 0.1% Tween 20 three times for 20 minutes each. The protein band was visualized by using Western blotting luminol reagent (Santa Cruz Biotechnology, USA). The activity was analyzed by using Image J software (version 1.37, NIH, USA).

Figure 7:
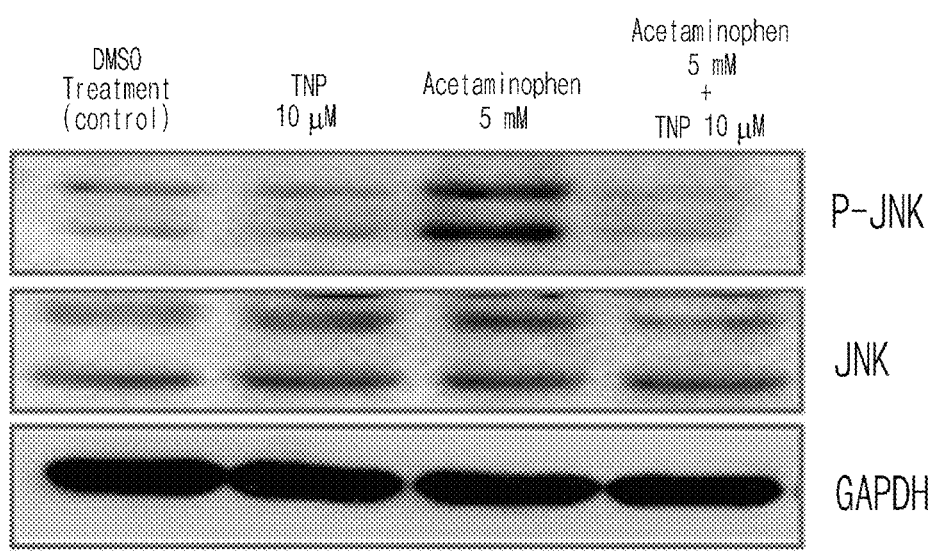
FIG. 7 is a diagram illustrating the JNK phosphorylation according to the treatment of acetaminophen and TNP in the mouse derived liver cells.

As a result, as shown in FIG. 7, it was confirmed that the phosphorylated JNK signal increased by the acetaminophen caused stress response was significantly suppressed by the treatment of TNP (FIG. 7).

Experimental Example 6: Suppression of JNK Phosphorylation Increased by Acetaminophen According to the Treatment of TNP in the Human Hepatoma Cell Line HepG2

The regulation of response against stress caused by acetaminophen in liver cells according to the treatment of TNP was investigated.

Particularly, the human hepatoma cell line HepG2 treated with acetaminophen and TNP by the same manner as described in Experimental Example 3 was obtained. Cell extract was prepared for protein assay. Then, SDS-PAGE and Western blotting were performed by the same manner as described in Experimental Example 5.

Figure 8:
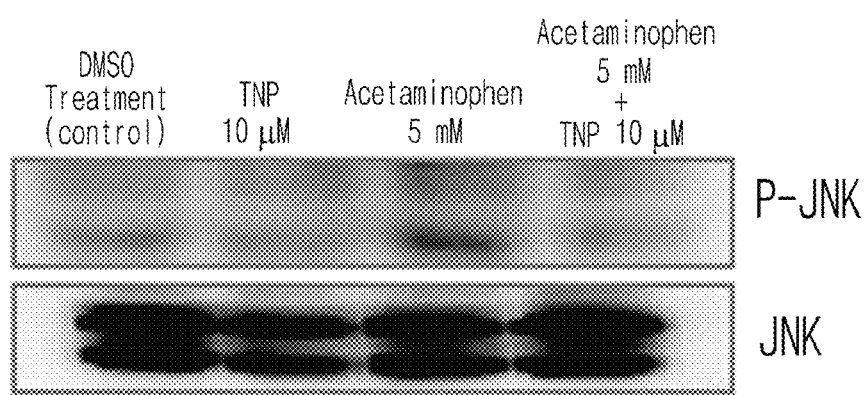
FIG. 8 is a diagram illustrating the JNK phosphorylation according to the treatment of acetaminophen and TNP in the human hepatoma cell line.

As a result, as shown in FIG. 8, it was confirmed that the phosphorylated JNK signal increased by the acetaminophen caused stress response was significantly suppressed by the treatment of TNP (FIG. 8).

Experimental Example 7: Analysis of Individual Survival Rate According to the Treatment of Acetaminophen and TNP in a Mouse Model The inventors investigated whether or not TNP had the activity of protecting liver cells from the toxicity caused by acetaminophen in an animal model.

Particularly, the male C57BL/6J mouse at 8~10 weeks was orally administered with 500 mg/kg of acetaminophen (Sigma) dissolved in water. Then, the mouse was administered with 10 mg/kg of TNP (Calbiocham) dissolved in olive oil (Sigma) via intraperitoneal injection, followed by investigation of individual survival rate. Statistical analysis was performed by Kaplan-Meier survival analysis, and the maximum limit of the significance was determined as $p<0.05$.

Figure 9:
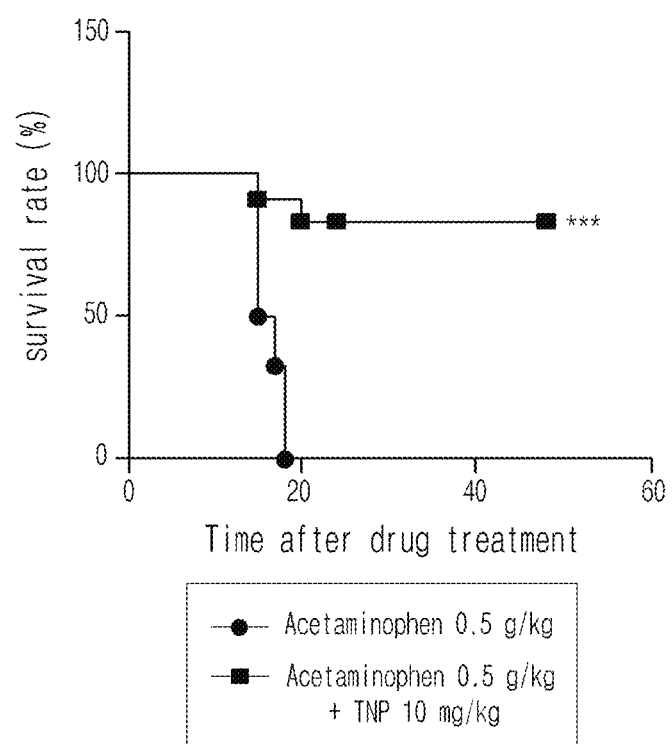
FIG. 9 is a diagram illustrating the individual survival rate according to the treatment of acetaminophen and TNP in the mouse model.

As a result, as shown in FIG. 9, it was confirmed that the TNP treatment had the effect of protecting a mouse from the acetaminophen caused liver toxicity, proved by the individual survival rate investigated above (FIG. 9).

Experimental Example 8: Analysis of Liver Toxicity According to the Treatment of Acetaminophen and TNP in a Mouse Model To investigate the preventing effect of TNP on the acetaminophen caused liver toxicity in the animal model of Example 7, tissues, blood, and JNK phosphorylation were analyzed.

Particularly, acetaminophen and TNP were injected to the male mouse by the same manner as described in Example 7. 6 hours later, the liver was extracted from the mouse, followed by histopathological analysis, blood analysis (AST and ALT), and stress signaling activity (JNK) analysis. For the blood analysis, a blood sample was obtained from orbit of the mouse. The blood sample was centrifuged at 13,000 rpm for 10 minutes to obtain serum. AST and ALT analysis was performed (Idexx VetTest 8008 chemistry analyzer) with 100 µl of the serum obtained above. To investigate the stress signaling activity, the liver tissues extracted from the liver taken out above were loaded in RIPA medium (1 M tris-Cl (PH7.4), 1 M NaCl, 0.5 M EDTA, NP-40, 10% sodium deoxycholate, 10% SDS), followed by lysis with a homogenizer. After the centrifugation, the supernatant was collected, followed by SDS-PAGE and Western blotting. The phosphorylated JNK and the total JNK were quantified by Western blotting by the same manner as described in Example 5.

Figure 10:
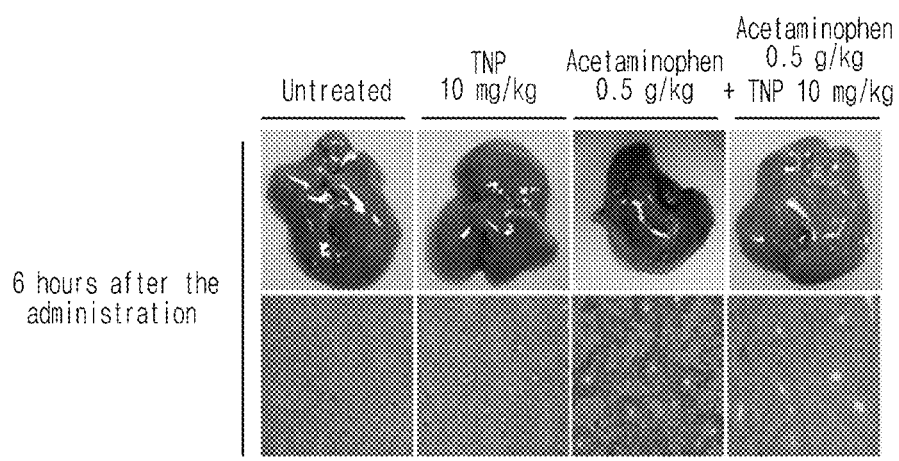
FIG. 10 is a diagram illustrating the result of histopathological analysis according to the treatment of acetaminophen and TNP in the mouse model.
Figure 11:
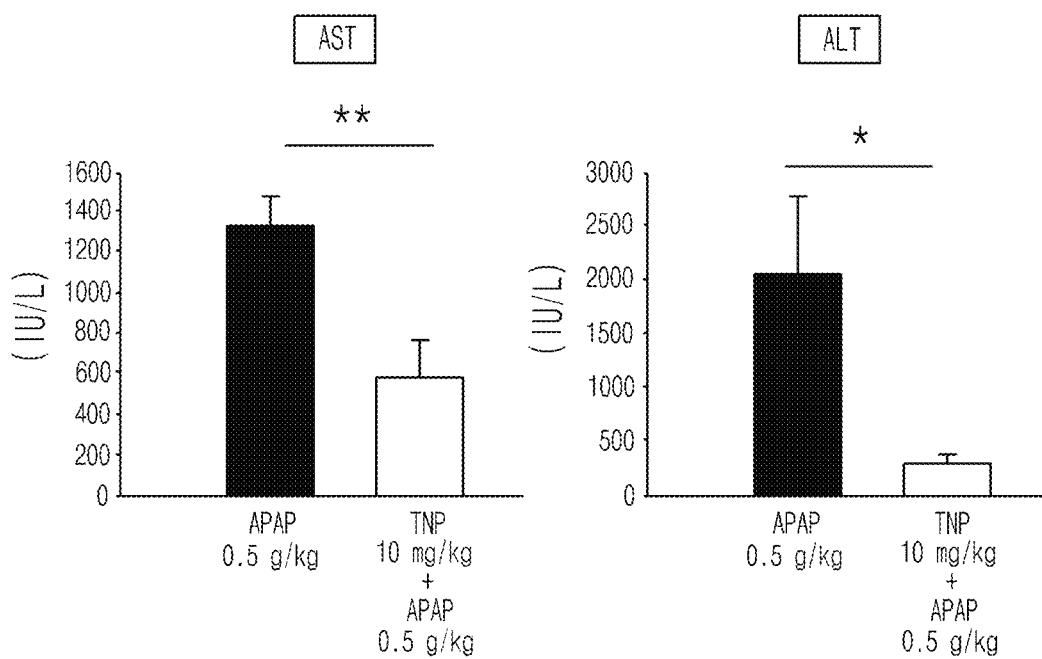
FIG. 11 is a diagram illustrating the result of blood analysis according to the treatment of acetaminophen and TNP in the mouse model.
Figure 12:
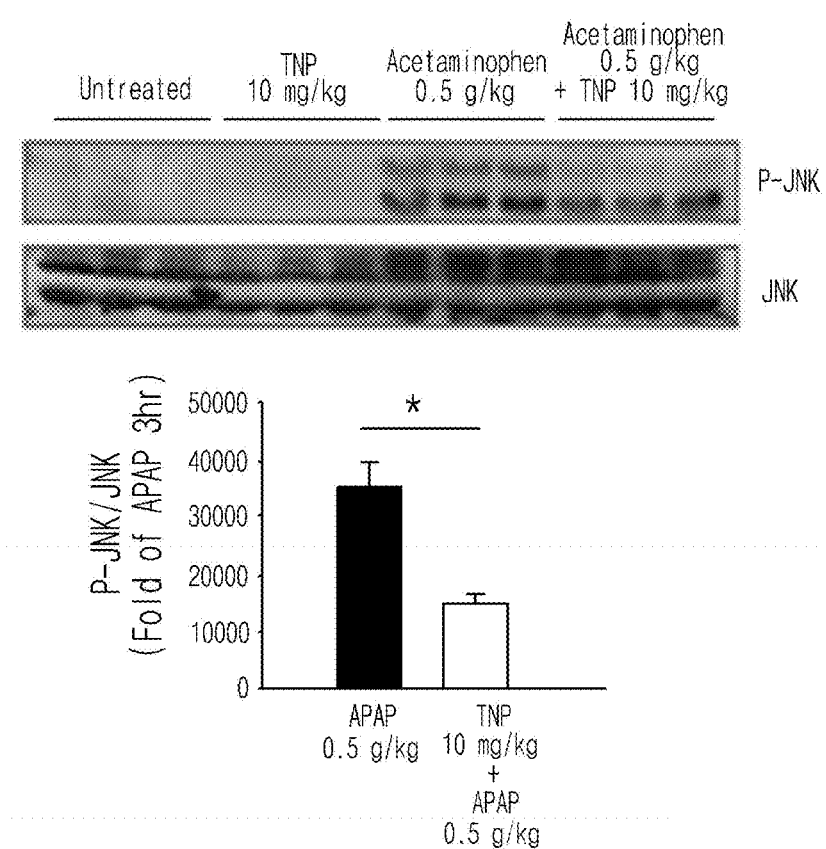
FIG. 12 is a diagram illustrating the JNK phosphorylation according to the treatment of acetaminophen and TNP in the mouse model.

As a result of the histopathological analysis with the liver tissue treated with acetaminophen, as shown in FIG. 10, only minor necrosis was observed in the mouse liver tissue treated with TNP along with acetaminophen (FIG. 10). As shown in FIG. 11, the levels of AST and ALT, the liver toxicity serum indexes, were significantly decreased in the mouse treated with TNP along with acetaminophen (FIG. 11). As shown in FIG. 12, the increase of acetaminophen caused stress response resulted in the increase of phosphorylated JNK signal, but the increase of phosphorylated JNK signal was significantly suppressed by the treatment of TNP (FIG. 12).

Therefore, it was confirmed by the liver tissue analysis using an animal model that TNP had the liver protecting effect from the liver toxicity caused by acetaminophen.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating liver toxicity comprising the step of administering a pharmaceutically effective dose of TNP (N2-(m-Trifluorobenzyl), N6-(p-nitrobenzyl)purine) or a pharmaceutically acceptable salt thereof to a subject in need of treatment.

2. The method for treating liver toxicity according to claim 1, wherein said TNP is the compound represented by the following formula 1:

[Formula 1]

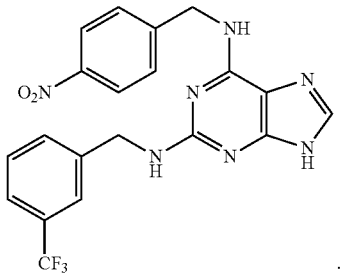

3. The method for treating liver toxicity according to claim 1, wherein said TNP suppresses apoptosis caused by acetaminophen (AP).

4. The method for treating liver toxicity according to claim 2, wherein said TNP increases the level of glutathione (GSH) in liver cells.

5. The method for treating liver toxicity according to claim 1, wherein said TNP suppresses a stress response increased by acetaminophen.

6. A method for treating liver disease comprising the step of administering a pharmaceutically effective dose of TNP (N2-(m-Trifluorobenzyl), N6-(p-nitrobenzyl)purine) or a pharmaceutically acceptable salt thereof to a subject in need of treatment.

7. The method for treating liver disease according to claim 6, wherein the liver disease is selected from the group consisting of fulminant hepatic failure, liver necrosis, nephrotoxicity, and liver cirrhosis.

* * * * *